United States Patent [19]

Müller

[11] 4,105,550

[45] Aug. 8, 1978

[54] PREPARATION OF STERILE PRODUCTS

[76] Inventor: Hans Müller, Im Allmendli, Erlenbach, Zurich, Switzerland

[21] Appl. No.: 607,875

[22] Filed: Aug. 26, 1975

Related U.S. Application Data

[63] Continuation of Ser. No. 428,345, Dec. 26, 1973, abandoned.

[30] Foreign Application Priority Data

Dec. 23, 1972 [CH] Switzerland .................. 18976/72

[51] Int. Cl.$^2$ ............................................. B01D 17/00
[52] U.S. Cl. ...................................... 210/50; 210/65; 210/68
[58] Field of Search .................. 210/50, 330, 332, 342, 210/415, 501, 65, 68

[56] References Cited

U.S. PATENT DOCUMENTS 3,233,734  2/1966  Müller ..................................... 210/68

OTHER PUBLICATIONS

Remington's Pharmaceutical Sciences, Mortin, 13th Ed., 1965, Mack Pub. Co., pp. 516–517, 478–479, 365–366, 332–333.

Primary Examiner—Charles N. Hart
Assistant Examiner—Ferris H. Lander
Attorney, Agent, or Firm—Michael J. Striker

[57] ABSTRACT

A sterile product is to be prepared from a substance which is dissolved in a solution. The first step in the preparation consists of subjecting the solution to a sterilizing filtration. Thereafter, the substance dissolved in the solution is precipitated therefrom under sterile conditions and the precipitate separated from the filtrate by means of a rotary disc filter which is located in a previously sterilized, closed chamber. Subsequent to the filtration, a dry, sterile gas is passed through the precipitate on the filter to dry it and the filter is then set into rotation so that a centrifugal force acts on the precipitate and causes it to be removed from the filter. The resulting product, which is completely sterile, is then immediately placed in a container. An arrangement for carrying out the above process is also disclosed.

4 Claims, 1 Drawing Figure

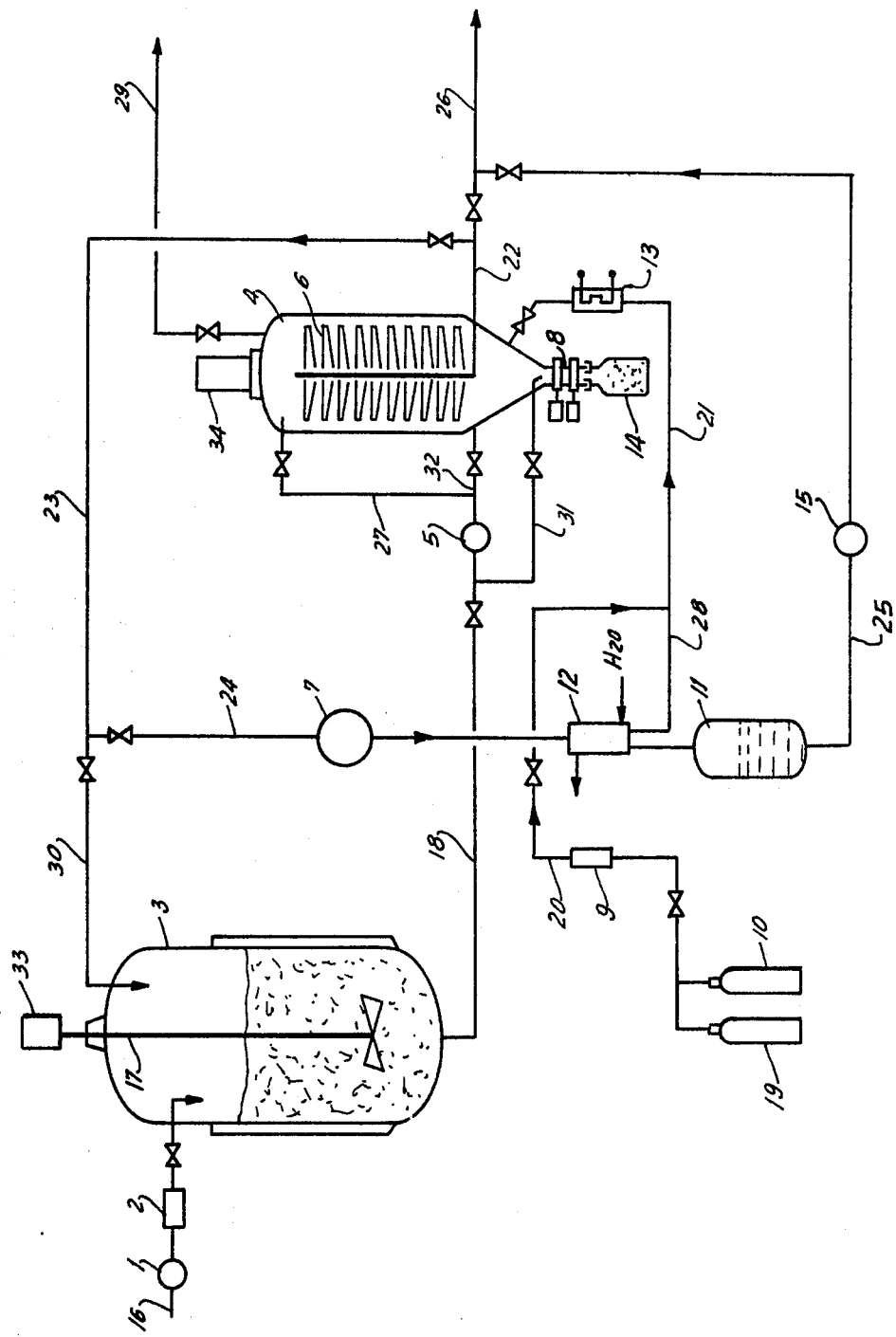

PREPARATION OF STERILE PRODUCTS

CROSS-REFERENCE TO RELATED APPLICATION

This application is a continuation of my application Ser. No. 428,345, filed Dec. 26, 1973, now abandoned.

BACKGROUND OF THE INVENTION

The invention relates generally to a process and arrangement for the preparation of sterile products and, more particularly, to the preparation of sterile products from substances dissolved in solution.

In industrial processing, it is often necessary to produce substances in the form of dried goods which are absolutely sterile. This is particularly true for pharmaceutical products and foods and also for other products. Such a preparation is relatively simple in those cases where it is possible to subject the end product to an elevated temperature which is sufficiently high to kill all of the microorganisms which are present. However, if it is not possible to subject the end product to such an elevated temperature as, for example, in the case of antibiotics and other substances which are susceptible to elevated temperatures, then the preparation of a sterile product not only becomes many times more expensive but very often the sterilization is incomplete. For instance, the sterilization of antibiotics which, as end products, exist in crystalline form can be accomplished only with great difficulty and, moreover, the sterilization is incomplete. The reason is that temperatures in excess of about 50° or 60° C cause destruction of these substances or adversely influence them. Although it is possible to work in sterile chambers and to provide protection for the personnel so as to prevent contamination of the substances by them, such procedures are only partially effective and, in addition, are very expensive.

It will be seen that the heretofore used processes and arrangements for preparing sterile products require improvement.

SUMMARY OF THE INVENTION

It is, accordingly, a general object of the invention to provide a novel process and arrangement for the preparation of sterile products.

More particularly, it is an object of the invention to provide a process and arrangement for the preparation of sterile products from substances which are dissolved in a solution and are precipitated therefrom.

Still more specifically, it is an object of the invention to provide a process and arrangement whereby it is possible to reliably obtain absolutely germ-free or sterile products from substances which are dissolved in a solution and which must be precipitated or crystallized and subsequently subjected to a filtration and dried.

Another object of the invention is to provide a process and arrangement for the preparation of sterile products from substances which are dissolved in a solution whereby the sterile products may be obtained in a simple and uncomplicated manner.

An additional object of the invention is to provide a process and arrangement for the preparation of sterile products from substances which are dissolved in a solution whereby the sterile products may be obtained inexpensively.

In accordance with the foregoing objects and others which will become obvious, the invention provides, in a process for preparing a sterile product from a substance which is dissolved in a solution and is precipitated therefrom, for subjecting the solution to a sterilizing filtration prior to precipitation of the dissolved substance from the solution. An arrangement for preparing a sterile product from a substance which is dissolved in a solution and is precipitated therefrom includes means defining a flow path for the solution and means in this flow path for effecting precipitation of the dissolved substance from the solution. The arrangement further comprises means for effecting a sterilizing filtration of the solution, the latter means also being provided in the flow path for the solution and being upstream of the precipitation effecting means.

According to the invention, the solution may be conveyed into a sterile precipitating apparatus subsequent to the sterilizing filtration. The precipitation may be a straight precipitation, a crystallization or both. After being precipitated, the originally dissolved substance, which is now present in solid form, may be separated from the liquid by filtering in a closed, previously sterilized filtering system. The precipitated substance may then be dried with a germ-free or sterile gas and immediately packed into a sterile container.

The germ-free or sterile filtration of the solution, that is, the sterilizing filtration, may be carried out with an asbestos layer filter or with a membrane or diaphragm filter. After the sterilizing filtration, the solution may flow into a closed preparation plant which is sterilized with steam, a heated gas, other heating means or chemically prior to the process, that is, before the solution is admitted therein. Such a plant includes tanks or containers for precipitation or crystallization, a filtering apparatus with means for circulation of a sterile drying gas, a condensing apparatus for the removal from the gas of the liquid picked up thereby and which has been vaporized, means for heating the gas and means for evacuating the dry product in a sterile manner. By pumping the suspension, that is, the mixture obtained by the precipitation and which includes the precipitated substance and the solvent for this substance, through the filter, removing residual liquid from the filter by means of a gas under pressure or by means of a pump, and drying the precipitate using a circulating gas, it is possible to pack the product into the container therefor without any contact between the product and the surroundings and in an absolutely sterile manner.

For separating the precipitated or crystallized substance from the suspension and for drying the precipitated substance, it is advantageous to use a rotary disc filter whose elements or discs are provided with a filtering medium or web only on the upwardly facing surfaces thereof and which may be set into rapid rotation for the purpose of removing the filter cake therefrom. Such forms of filters have the advantage that both the filtration and the drying with an inert gas may be undertaken in a closed system or circuit so that it is a simple matter to maintain the apparatus in sterile condition. In contrast, when filter presses or vacuum filters are used, the possibility of an infection from an external source exists. Also, when using filters wherein the filter surfaces are vertically oriented (for example, filter candles or plate filters), the filter cake, that is, the precipitated or crystallized substance, does not cling to the filter surfaces so that it becomes difficult to carry out the drying operation in the filter itself. It is for these reasons that the process in accordance with the invention is advantageously carried out with a rotary disc filter as above.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWING

The single FIGURE is a diagrammatic representation of an arrangement for carrying out the process according to the invention.

DESCRIPTION OF THE PREFERRED EMBODIMENTS

Referring now to the drawing, it may be seen that this schematically illustrates an arrangement for the preparation of sterile products such as, for instance, antibiotics. A substance in dissolved form, that is, a solution of the substance in an appropriate solvent, is pumped into a sterilizing filter 2 by a pump 1 via a conduit 16. After passing through the filter 2, the substance is further pumped by the pump 1 into a precipitation or crystallization tank 3. Here, the dissolved substance is precipitated out of the solution thereby forming a mixture or suspension which includes the substance in solid form and the solvent for the substance. The precipitation may involve crystallization of the substance. It may be seen that the tank or container 3 is provided with a stirrer 17 which is driven by a suitable motor 33.

After the precipitation, the slurry containing the solid precipitate or crystals is conveyed from the tank 3 to a filter 6 which is here illustrated as being a rotary disc filter. A pump 5 conveys the slurry from the tank 3 to the filter 6 via the conduits 18 and 32. The filter 6 is located in a closed chamber or housing 4. The precipitate conveyed to the filter 6 settles on the plates or discs thereof. The filtrate is returned from the filter 6 to the precipitation tank 3 via the conduit 22, 23 and 30. This circulation of the filtrate continues until all of the plates of the filter 6 are covered with precipitate and the liquid coming from the filter 6, that is, the filtrate, is free of suspended matter. Instead of circulating the filtrate between the filter 6 and the tank 3, it is also possible to remove part or all of the filtrate from the system during the filtration.

Subsequent to the filtering operation, that is, after the precipitated substance and the solvent for the substance have been separated, residual filtrate is removed from the filter 6 either by means of a pump or by means of a sterile gas under pressure. Then, sterile air or some other gas is circulated through the still damp filter cakes present on the plates of the filter 6. The air or gas may be supplied, respectively, from the souces 19 and 10 althouh, where air is used, this may also be supplied from the atmosphere rather than from the source 19. The gas may, for instance, be an inert gas such as nitrogen. The air or gas passes through a conduit 20 in which there is provided a sterilizing filter 9 and then continues on into the conduit 21. Suitable means are, of course, provided for conveying the air or gas through the conduits 20 and 21 although these are not illustrated for the sake of clarity. It is also possible for the sources 19 and 10 to pressurize the air or gas for conveying these through the conduits 20 and 21. It will be seen that a heater 13 is provided in the conduit 21 for heating the air or gas prior to admission into the chamber 4 wherein the filter 6 is located. The heater 13 may, for example, heat the air or gas to a temperature of 60°–70° C. The heated air or gas passes through the damp filter cakes or precipitate on the plates of the filter 6 thereby drying the same. After passing through the filter 6, the air or gas leaves the chamber 4 via the conduit 22 and flows through the conduits 23 and 24 to a cooler or condenser 12. Here, the air or gas is cooled, for instance, to a temperature of 0° C. The filtrate or solvent condenses in the condenser 12 so as to become separated from the air or gas and the condensed filtrate then passes into a container 11 from where it may be withdrawn, via a conduit 25, for further use by a pump 15. The thus-recovered filtrate may be returned to the tank 3 via the conduit 26. As indicated by the arrows, water may be circulated through the condenser for cooling purposes.

When air is used for drying the precipitate on the filter 6, it is not necessary to recirculate this. On the other hand, when using an inert gas for this purpose, it is advantageous to recirculate the gas. Any suitable means may be used for recirculating the gas and, in the present instance, the recirculating means is shown as being in the form of a blower 7. Thus, gas which has passed through the filter 6 and has been conveyed into the condenser 12 leaves the latter via a conduit 28 communicating with the conduit 21 which, in turn, leads to the filter 6.

After drying of the precipitated substance with sterile air or gas, a vacuum may be applied at the top of the chamber 4 or the filter 6 by means of the vacuum line 29. This provides a final drying for the precipitated substance and insures that it is completely dry so that a dry, sterile product is obtained.

Subsequent to final drying of the precipitated substance, the filter 6 may be set into rotation by activating a motor 34. As a result, the dry product on the filter 6 is subjected to a centrifuging action, that is, the action of a centrifugal force, and is thereby removed from the filter 6. Valve means or an air lock 8 is provided between the filter 6 and a sterile receiving container 14 is opened so that the dry, sterile product may be packed into the latter and confined therein. Once the product has been confined in the container 14, that side of the sterile air lock 8 nearest the container 14 is closed and the sterile product may then be removed. Of course, if the filter 6 is not of the rotatable type, other suitable means for removing the dry, sterile product from the filter will be provided.

It will be understood that the arrangement is suitably sterilized before the solution containing the dissolved substance is admitted therein. This may be accomplished by passing a heated gas through the arrangement or by passing steam under pressure through the arrangement. The steam may, for example, have a temperature between 120° and 130° C. Of course, the tank 3, the chamber 4, the filter 6 and the air lock 8 are all included in this sterilization. The prior sterilization of the arrangement insures that the various operations are carried out under sterile conditions.

It will be appreciated that by providing for a sterilizing filtration of the solution before precipitation of the substance therefrom, the invention has obviated the need for heating the end product to an elevated temperature which may adversely affect the same.

It is pointed out here that the details of the operation of the various valves illustrated have not been described since their operation is self-evident. Moreover, it will be seen that the arrangement includes conduits 31 whose purpose is to provide for recirculating the filtrate from the bottom of the filter 6 to the top thereof so as to wet the filter cake on the plates therein. This can be effected by shutting the valves represented in the drawing that control the flow through conduits 18 and 32 and opening the valves that control the flow through conduits 27 and 31.

It will be understood that each of the elements described above, or two or more together, may also find a useful application in other types of processes and arrangements differing from the types described above.

While the invention has been illustrated and described as embodies in the preparation of sterile products, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims:

1. A process for obtaining a solid pharmaceutical substance in sterile form comprising the steps, in succession, of
    (1) passing a solution of the substance through a sterilizing filter;
    (2) then passing the sterilized solution directly from the sterilizing filter into a presterilized precipitation tank where the solution is brought in contact with a precipitating medium so as to form a solids-containing suspension;
    (3) thereupon passing the suspension directly from the precipitation tank to a presterilized rotary disk filter where the solids are deposited on the disks as filter cake while the liquid medium is passed out of the filter as the filtrate;
    (4) continuously recycling said filtrate into said precipitation tank until it is free of all residual solids;
    (5) passing a heated inert gas or heated air through a sterilizing filter and thereafter into the rotary disk filter to completely dry said filter cake;
    (6) then passing the wet gas or air out of the filter and into a condenser where the residual filtrate is separated from the gas or air;
    (7) continuously recirculating the recovered gas, into the precipitation tank;
    (8) applying a vacuum to the disk filter to complete the drying;
    (9) subjecting the filter disks to a centrifugal action whereby the deposited solid substance constituting the said filter cake is detached from said disks of the rotary filter, and
    (10) finally passing the separated sterile, completely dry solid substance out of the disk filter and into a presterilized collection vessel for future use, all passages between said sterilizing filter, precipitation tank, rotary disk filter, gas or air sterilizating filter and collection vessel as well as all recirculation ducts between said disk filter and precipitation tank and between the disk filter, condenser and precipitation tank being sterilized prior to the operation, and the said sterilizing filter for the solution, precipitation tank, disk filter, gas or air filter and collection vessel together with connecting ducts thus forming a closed sterile system.

2. A process as defined in claim 1 in which the heated air or inert gas is at a temperature between 60° and 70° C.

3. The process of claim 1 wherein the removal of the liquid filtrate from the separating tank is effected by pump means or a pressurized gas prior to passing said heated air or gas through the separating filter.

4. A process as defined in claim 1 in which the pharmaceutical substance is an antibiotic.

* * * * *